United States Patent [19]
DeGunther et al.

[11] Patent Number: 5,373,367
[45] Date of Patent: Dec. 13, 1994

[54] MULTIPLE ANGLE AND REDUNDANT VISIBILITY SENSOR

[75] Inventors: Richard N. DeGunther, Cameron Park; Wilbert I. Marsh, Orangevale, both of Calif.

[73] Assignee: Qualimetrics, Inc., Sacramento, Calif.

[21] Appl. No.: 964,365

[22] Filed: Oct. 21, 1992

[51] Int. Cl.⁵ ............................................. G01N 21/59
[52] U.S. Cl. .................................... 356/438; 356/337; 356/338; 356/339; 356/73; 356/435; 356/340; 356/342; 356/386; 356/387
[58] Field of Search ............... 356/438, 337, 338, 339, 356/340, 342, 343, 435, 386, 387, 73

[56] References Cited

U.S. PATENT DOCUMENTS 2,788,702  4/1957  Baum .................................... 356/340
4,594,581  6/1986  Matoba .................................. 356/438

FOREIGN PATENT DOCUMENTS

0022932  3/1981  Japan .................................... 356/438

*Primary Examiner*—David L. Willis
*Assistant Examiner*—LaCharles Keesee
*Attorney, Agent, or Firm*—Fliesler, Dubb, Meyer & Lovejoy

[57] ABSTRACT

A multiple angle and redundant visibility sensor includes a plurality of optical transmitter/receiver pairs, each pair cooperatively coupled so as to transmit and receive in conically controlled beams along a common optical axis such that each transmitter faces, and directs optical energy directly into, its receiver pair. The plurality of pairs are staggered in angular orientation with respect to each other, with a common volume of intersection through which the approximate center of each optical axis passes. Each transmitter propagates a substantially conical beam of light which passes through an aerosol media which causes molecular scattering of the light. A single transmitter outputs optical energy at any given time, and the receiver intercept the appropriate scattered energy at different scattering angles depending on the relative axial orientation with respect to the scattering volume and the incident radiation. Automatic calibration is effected by measuring the transmission properties through the forward beam, or between cooperating pairs of transmitters and receiver elements. The various scattered energies are then compared to this direct path intensity to obtain the appropriate angular scattering coefficients. Redundant transmit/receive pairs increase the system reliability as well as data validity.

26 Claims, 8 Drawing Sheets

MULTIPLE ANGLE AND REDUNDANT VISIBILITY SENSOR

BACKGROUND OF THE INVENTION

1. Field of the Invention

This invention relates to visibility sensors. In particular, this invention relates to visibility sensors which are capable of measuring scattering amplitudes at different scattering angles. Multiple head redundancy ensures a higher degree of reliability, accuracy and self calibration.

2. Description of the Prior Art

In the most common type of application for a visibility sensor, the measurement parameter of interest is ultimately the extinction coefficient, which essentially gives the amount of attenuation that will be experienced by a light beam as it travels through an aerosol medium, such as atmospheric air. The extinction coefficient is related to the scattering coefficient through a complicated extinction integral which includes the scattering coefficient as a parameter. Visual range is the distance which a human observer will be able to see under certain background lighting conditions. Other factors, such as contrast, appear in the visibility range equation, but the major difficulty in determining visual range is in the visibility measurement. The visibility measurement is independent of the background lighting and is only a function of the total scattering within the atmosphere. An inexpensive and accurate means of reliably measuring this value is needed.

There are a wide range of prior art devices intended to measure the extinction coefficient of an aerosol. The forward scatter method offers several distinct advantages. In forward scatter meters the receiver accepts light from a source which has been scattered in a near-forward direction. The scattering coefficient in the direction of an angle of approximately 150 degrees between the axis of the beam and the axis of the receiver is nearly independent of the particle size distribution of the aerosol. For other angles, the ratio of the wavelength of optical energy used to probe the sample, to the size of the particles in the aerosol causes variations in the angular scattering coefficient for a given aerosol. Several regimes of size ratios are addressed in current theoretical literature.

Forward scattering meters are less sensitive to the particle size than backscatter meters or conventional linear path transmissometers. In addition, the total scattering coefficient is much greater in a general forward direction than a backward direction, and this manifests itself in an appreciably higher signal to noise ratio at the optical receiver. This translates, in turn, to a better sensitivity specification for forward scatter devices compared to other devices in the prior art.

U.S. Pat. No. 4,432,645 (Frungel, et al.) discloses a forward scatter visibility meter which includes a transmitter and a receiver which cooperatively couple at an obtuse forward scatter angle. The disclosure describes a calibration means which is used to measure the direct path light propagation characteristics of the aerosol media. This method will accountably modify the measurement process for dirty windows, aging light emitting elements and other factors which affect the overall through-path optical energy amplitude. By comparing the scattered amplitude with the direct path amplitude, a ratio is obtained which directly relates to the angular scattering coefficient at the angle indicated by the invention. It is designed to eliminate the effects of dust particles on transmitter and receiver windows on the measurement results. The transmitter beam direction is inclined downwards and the receiver direction of reception is inclined at an obtuse angle to the transmitter, also inclined downward; this reduces the noise level due to background scattered atmospheric optical energy. The invention includes an aperture with rain guiding ridges in order to keep raindrops from entering the active scatter volume which is comprised of the volume of aerosol within the intersection of the transmitter cone and the receiver cone. The calibration methodology disclosed requires manual intervention and an operator must occasionally service the unit in order to exploit the disclosed method.

U.S. Pat. No. 4,099,875 (McMahon, et al.) discloses an apparatus which determines the scattering coefficient of an aerosol media by measuring the amount of backscattered light. An optical transmitter beams optical energy into an aerosol medium and the backscattered light is measured in a time selective manner so that near and far field estimations may be made. A complicated processing phase is needed in order to turn the backscattered data into forward extinction coefficient data.

U.S. Pat. No. 4,329,054 (Bachalo) discloses a method of sizing aerosol particles by using laser light. A laser generator produces a pair of coherent laser beams of the same wavelength and intensity. These beams are directed and focused by focusing means along a first axis, and caused to cross at this first axis to establish an interference pattern. A collector for sensing the scattering caused by the particles in the interference pattern has a probe axis extending into the interference pattern. This probe axis is off-axis from the first axis. The visibility is determined from the information sensed by the collector. A sizing device for establishing the size of a particle, droplet or the like from the visibility is coupled to the visibility determining device and provides an output signal representative of the size. This apparatus uses a single frequency of optical energy.

U.S. Pat. No. 4,362,387 (Clark) discloses an invention for measuring the visibility of daylight by using polarization properties of sky and atmospheric light scattering. The intensities of two mutually perpendicular and linearly polarized components of the daylight are measured so that a polarization ratio can be calculated to provide a visibility index by which visual quality and visual range can be determined. Alternatively, the polarization properties at ultraviolet and infrared regions of the electromagnetic spectrum may be used in order to determine a three-dimensional topographical characterization of the sky. This apparatus is useful for remote types of observations, but is extremely expensive to facilitate and calibrate.

As seen above, prior art devices have attempted to characterize the scattering coefficients in various ways. Scattered light undergoes certain polarization phenomenon, and several prior art devices have attempted to exploit this phenomenon. These devices suffer the disadvantage of being extremely complex and expensive. The signal to noise ratios at the receivers to these devices suggest a very poor overall accuracy level. Linear line transmissometers suffer the disadvantage of being very difficult to calibrate. This is because they attempt to obtain a ratio between transmission in an unattenuating vacuum path, with that transmission obtained through the appropriate aerosol medium. There is essentially no adequate method of achieving this said vacuum path.

Furthermore, multiple frequency light sources, which study the variation on angular scattering coefficient with respect to optical energy wavelength suffer the disadvantage of being extremely complex since optical devices tend to operate at preferred, narrow-band frequencies. Complicated arrays of prisms and beam splitters are therefore required and the alignment and maintenance become prohibitive and unreliable.

Thus, prior art visibility sensors suffer the disadvantage of requiring special calibration means to measure the direct path light transmission properties and do not measure the angular scattering coefficient at several different angles. In sum, a visibility sensor with improved accuracy variability and reliability is desired without added expense or complexity.

SUMMARY OF THE INVENTION

It is therefore a primary object of the present invention to provide a visibility sensor apparatus which will measure the forward angular scattering coefficient with an improved degree of accuracy, variability and reliability.

An object of the present invention is to provide a means to measure forward scatter parameters which will allow dirt and various degrading contaminants to reside on the optical surfaces of the invention without degrading the accuracy or reliability of the invention.

Another object of the present invention is to provide a means which will allow simultaneous and accurate measurements of different scattering angles without mechanically moving any parts of the system.

Still another object of the present invention is to provide a means which will be capable of operation with one or more elements of the system in a condition of catastrophic failure.

Still another object of the present invention is to provide a means of increasing the accuracy of the forward scatter coefficient calculation by yielding a statistical sample of equivalent readings from different and independent sources. This feature will have the additional advantage of allowing the system to check itself, and to indicate to an operator whether the output data is viable or is suspect.

Still another advantage of the present invention is to provide a means of studying the particle size distribution of an aerosol medium by obtaining angular scattering coefficients at various scattering angles.

Briefly stated, and in accord with one embodiment of the invention, a multiple angle and redundant visibility sensor includes a plurality of optical transmitter/receiver pairs, each pair cooperatively coupled so as to transmit and receive in conically controlled beams along a common optical axis such that each transmitter faces, and directs optical energy directly into, its receiver pair. The plurality of pairs are staggered in angular orientation with respect to each other, with a common volume of intersection through which the approximate center of each optical axis passes. Each transmitter propagates a substantially conical beam of light which passes through an aerosol media which causes molecular scattering of the light. A single transmitter outputs optical energy at any given time, and the receivers intercept the appropriate scattered energy at different scattering angles depending on the relative axial orientation with respect to the scattering volume and the incident radiation. Automatic calibration is effected by measuring the transmission properties through the forward beam, or between cooperating pairs of transmitters and receiver elements. The various scattered energies are then compared to this direct path intensity to obtain the appropriate angular scattering coefficients. Redundant transmit/receive pairs increase the system reliability as well as data validity.

DESCRIPTION OF THE DRAWINGS

The invention is pointed out with particularity in the appended claims. However, other objects and advantages together with the operation of the invention may be better understood by reference to the following detailed description taken in connection with the following illustrations, wherein:

FIG. 1 represents a perspective view of the preferred embodiment of the present distributed element forward scatter visibility sensor invention.

FIG. 2 represents a block diagram view of the preferred embodiment of an optical receiver head of the present invention.

FIG. 3 represents a block diagram view of the preferred embodiment of an optical transmitter head of the present invention.

FIG. 4 represents a top view of a two receiver, redundant sensor configuration of the present invention.

FIG. 5 represents a top view of a two transmitter redundant sensor configuration of the present invention.

FIG. 6 represents a top view of the four-headed distributed element visibility sensor.

FIG. 7 represents a top view of the multiple scattering angle, redundant element visibility sensor system.

FIG. 8 represents a perspective view of a rotatable arm, multiple angle visibility sensor system.

DESCRIPTION OF THE PREFERRED EMBODIMENT

In order to better illustrate the advantages of the invention and its contributions to the art, a preferred hardware embodiment of the invention will now be described in some detail.

Referring now to FIG. 1, a multiple angle, redundant visibility sensor is comprised of an optical transmitter head 12, a second optical transmitter head 13, an optical receiver head 10 which is spatially configured so that its optical axis is coaxial to the optical axis of optical transmitter head 13, and a second optical receiver head 11 which is spatially configured so that its optical axis is coaxial to the optical axis of optical transmitter head 12. Optical receiver head 10 receives direct light from transmitter head 13, and scattered light from optical transmitter 12. Optical receiver 11 receives direct light from optical transmitter 12, and scattered light from optical transmitter 13. Support elements 14A through 14E provide mechanical rigidity and spatial alignment as shown in FIG. 1.

According to the commonly accepted standards in the meteorological industry, the angle separating the two optical axes is approximately 35 degrees. The appropriate angular scattering coefficient is obtained by taking the ratio of the direct transmitted light to the scattered intensity. This value will yield an indicator of the approximate visibility of the aerosol medium near the physical center of the four heads. This aerosol volume, near the center of the four heads, is intentionally kept well confined to a particular three-dimensional space, which necessitates adequate optical design for both the receiver heads and the transmitter heads.

Figure 1:
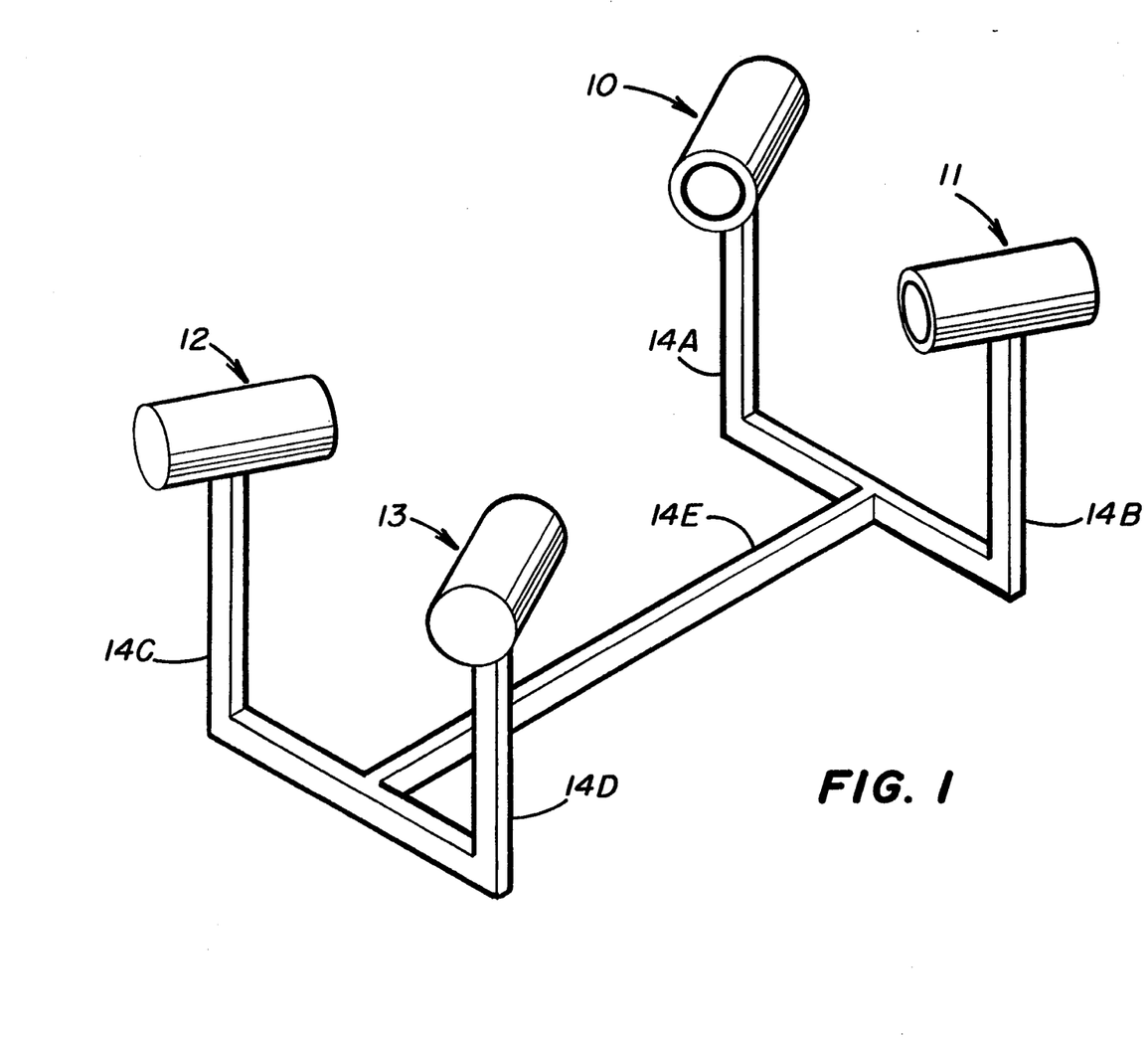

The system as shown in FIG. 1 is capable of complete operation in the event of a catastrophic failure of any of the four heads shown. Upon the event that optical receiver head 10 fails, the appropriate parameters may be measured by substituting values obtained from optical receiver head 11, in conjunction with optical transmitter head 12 and optical transmitter head 13. A like and symmetric situation applies to optical receiver head 11 failure. Upon the event that optical transmitter head 12 fails, the appropriate parameters may be measured by substituting values obtained from optical transmitter head 13 in conjunction with optical receiver head 10 and optical receiver head 11. A like and symmetric situation applies to an optical transmitter head 13 failure.

When all four optical heads are operating properly, the system yields two equivalent scatter coefficients, and the laws of statistics may be appropriately applied to these values to obtain a composite value which is of a higher order of confidence than the individual values. This, therefore, increases the accuracy of the present invention. The ability to operate under the conditions of a catastrophic failure of any optical head increases the reliability of the present invention.

In operation, the receiver heads are constantly operating, and the transmitter heads are toggled back and forth. Hence, a receiver head measures direct energy, then scattered energy, then direct energy, etc. A processor is normally used with the present invention to measure the results and control the toggling process, as well as interface with the end user of the system.

Figure 3:
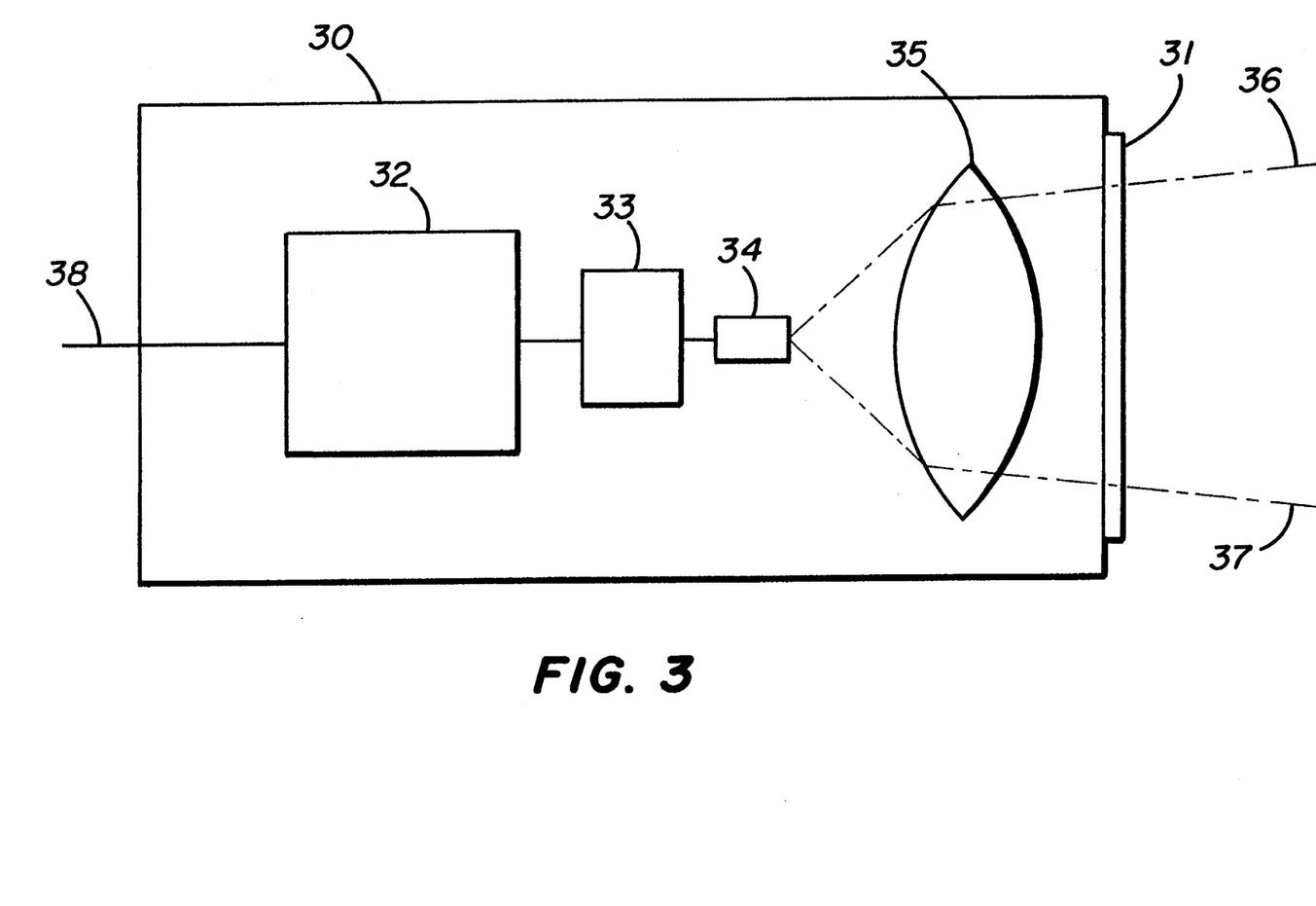

FIG. 3 shows a detailed block diagram of an optical transmitter head of the preferred embodiment of the present invention. The apparatus is contained within housing 30. In the preferred embodiment, housing 30 is generally cylindrical in shape, while other shapes may be used. Input window 31 allows the passage of the optical energy while providing a mechanical, weather-tight seal to housing 30. Lens 35 serves to collimate, or restrict, the light from optical light emitting diode 34. A laser could equally well be used in place of an optical light emitting diode without changing the essential features of the present invention. Light rays 36 and 37 define the limits of the light cone which is output from the optical transmitter head. The degree of collimation, or the amount of eccentricity of this light cone, is determined by considering the amount of overlap, or coupling, required between the receiver and transmitter. Power driver 33 supplies drive current to the optical light emitting diode 34. Modulator 32 provides an appropriate square wave modulation function to power driver 33. Control signal input 38 controls the state of the optical transmitter head.

Figure 2:
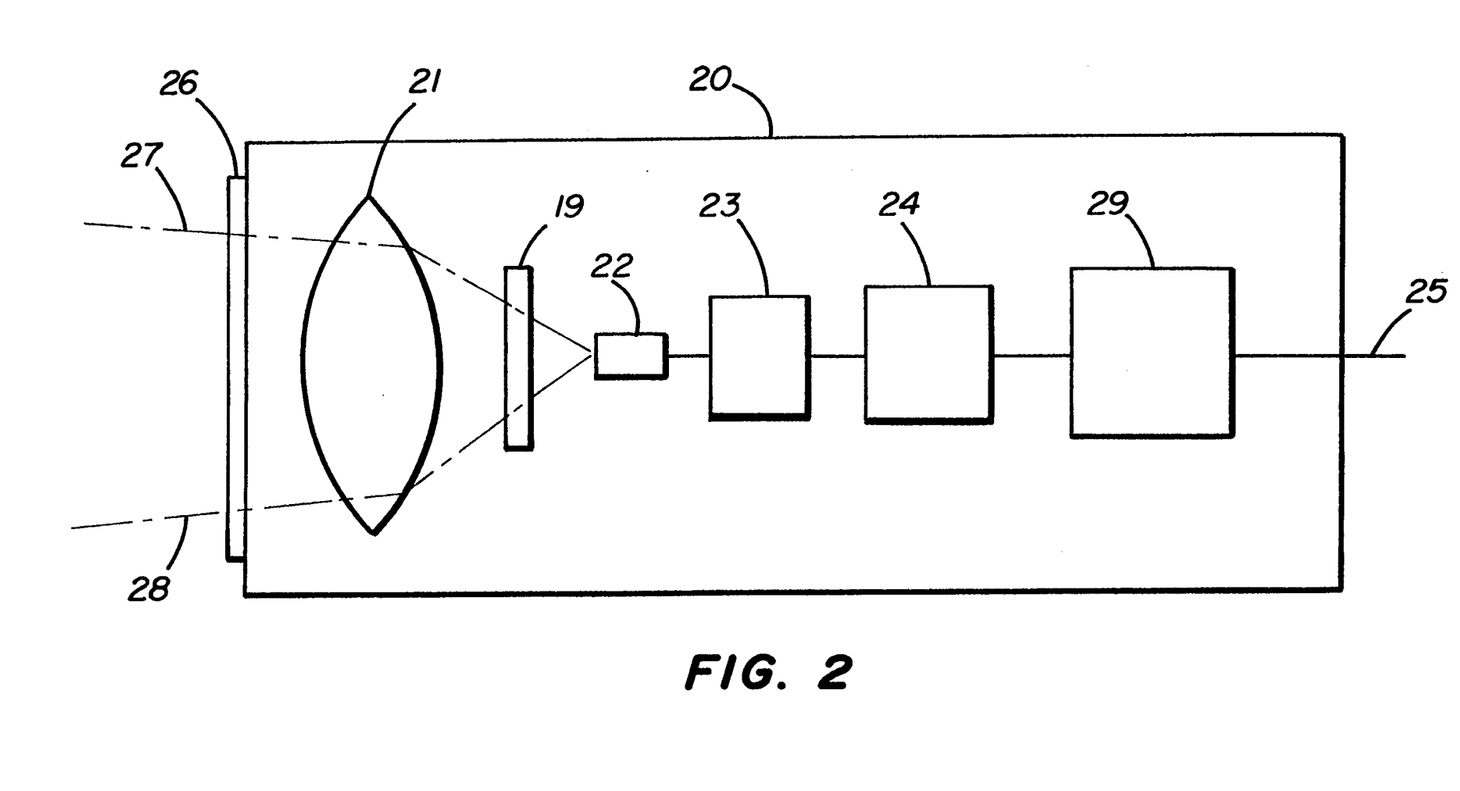

FIG. 2 shows a detailed block diagram of an optical receiver head. The apparatus is contained within housing 20, which in the preferred embodiment is generally cylindrical in shape. Optical window 26 provides an optically transparent seal to housing 20. Optical lens 21 focuses incoming light rays. Optical band pass filter 19 provides frequency discrimination which increases the effective signal to noise ratio of the system. Photo-diode 22 collects the incident photons and outputs an electrical signal in proportion to the intensity of the incident light energy. Electrical band pass filter 23 filters the input signal which is modulated with a square wave at a predetermined frequency. Rectifier/integrator 24 receives the signal from the electrical band pass filter 23, turns it into a full wave rectified signal and smooths this signal into a very constant DC voltage. Voltage to frequency converter 29 converts the DC output voltage from rectifier/integrator 24 into a square wave output which may be run over a very long cable length, in a very noisy environment to be read by a processor. Output 25 contains the appropriate square wave signal as output by the voltage to frequency converter 29.

Light rays 27 and 28 define the boundary of the input light cone which is incident upon photo-diode 22. The amount of collimation of the receiver light beam is given by the various quality factors of the optical components and is adjusted so as to give an appropriate overlap between the receiver beam and the transmitter beam.

In operation, the modulation frequency of the transmitter is tuned to match the electrical band pass filter transmission characteristics of the receiver. In this way, the signal to noise ratio is increased considerably. It is generally the case that the apparatus is operated in conditions of high background lighting, from the sun or from other background sources. The operation of the system must be immune to this background lighting. The modulation technique increases the immunity.

Figure 4:
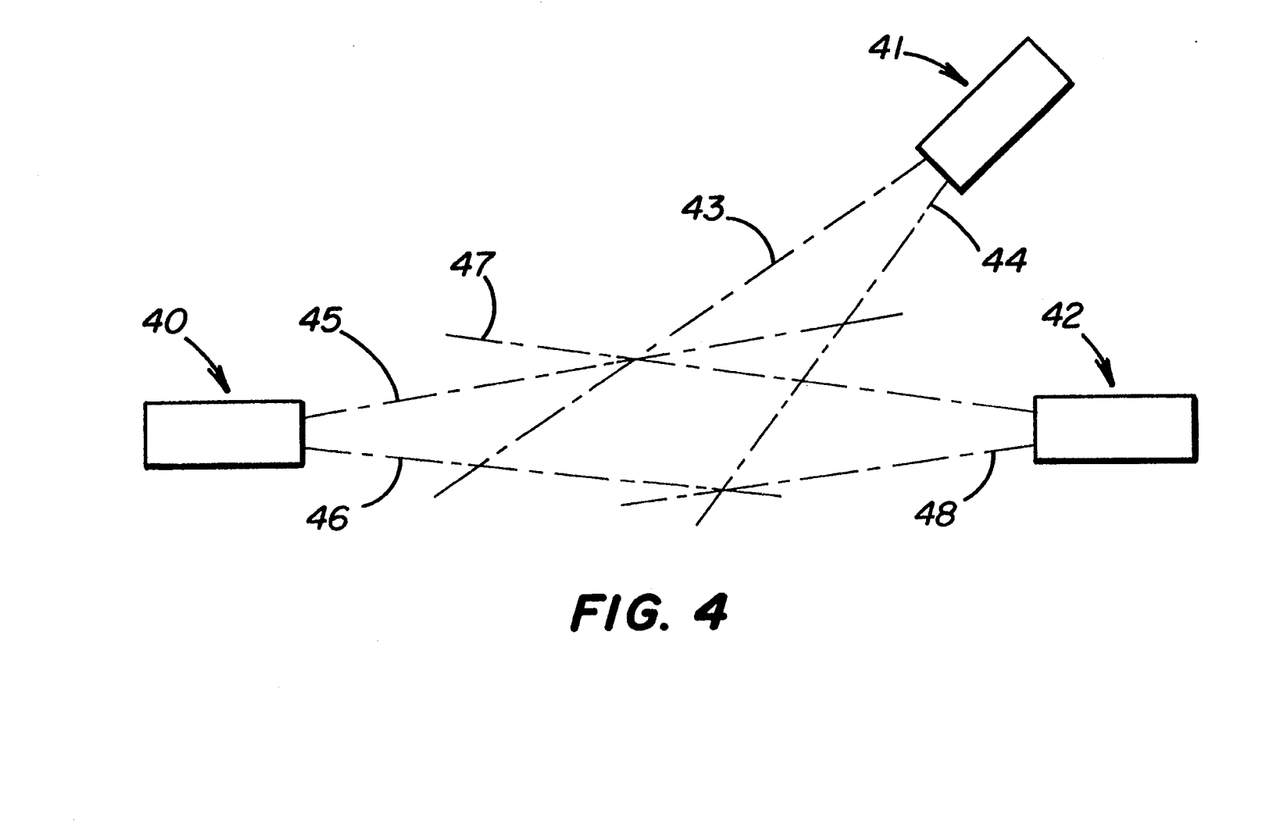

FIG. 4 shows a redundant receiver pair configuration in block diagram form. As described above, the receiver and the transmitter are configured to effect a conical transmit or receive beam shape. When the eccentricity of the cone is zero, the beam is essentially collimated, or pencil-shaped. FIG. 4 shows two-dimensional representations of the three-dimensional conical shapes and the intersecting regions defined by the light rays. One practiced in the art will be able to adequately visualize the three-dimensional structures, based on the two-dimensional representations presented.

Referring to FIG. 4, transmitter head 40 transmits a cone of light defined by light rays 45 and 46. The light is modulated with a square wave. Receiver light head 41 receives a conical pattern as defined by light rays 43 and 44, and receiver light head 42 receives a conical pattern as defined by light rays 48 and 47. The individual heads are aligned so that their light cones intersect in a substantially common volume, as shown in FIG. 4. Transmit light head 40 and receiver light head 42 are arranged coaxially, and receiver light head 41 is arranged at an obtuse angle from the common axis. The intersection volume represents the scattering volume, and the constituent particles in the aerosol within this volume provide the scattering targets. Secondary scattering may occur; however, this is much less probable and is generally discounted as an effect.

The calibration process works as follows. When the system is first turned on, the receiver and transmitter windows are cleaned and the direct amplitudes are measured between all pairs of receivers and transmitters. All subsequent measurements are compared to this amplitude in order to determine the amount of obfuscation. Next, the transmitters are all turned off, and the noise offsets are measured at each receiver. Finally, a predetermined scatter media is positioned at the point of the system scatter volume, and the scatter measurements at each receiver are measured. All subsequent measurements are then normalized by appropriate modifications derived from these three procedures. Periodic updating of the calibration numbers will be required.

Figure 5:
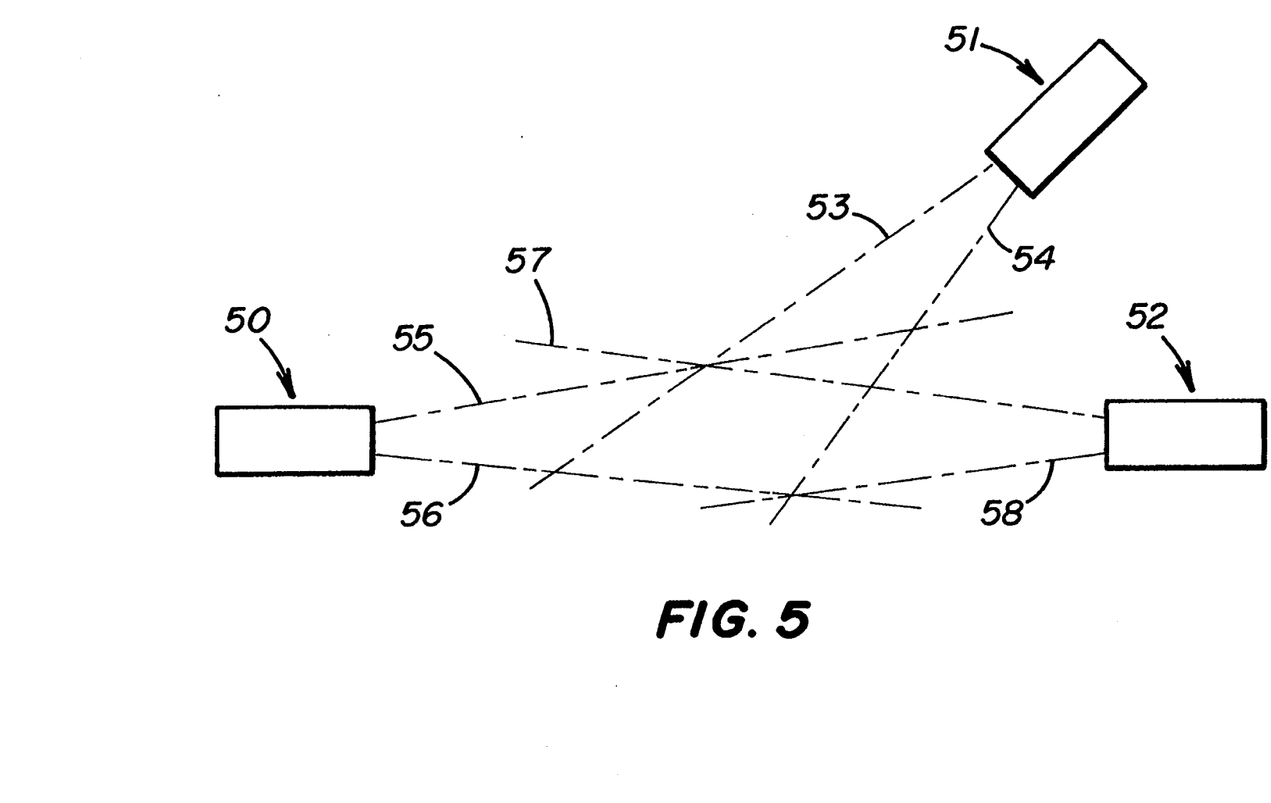

FIG. 5 shows a redundant transmitter pair configuration. Receiver head 50 is defined by light rays 55 and 56.

Transmit head 51 is defined by light rays 53 and 54, and transmit head 52 is defined by light rays 57 and 58. Receiver head 50 is arranged coaxially to transmit head 52, and transmit head 51 is arranged at an obtuse angle to the common axis between transmitter head 52 and receiver head 50. The individual elements are arranged so that there is a common volume of intersection of the individual light cones, as shown in the figure.

Figure 6:
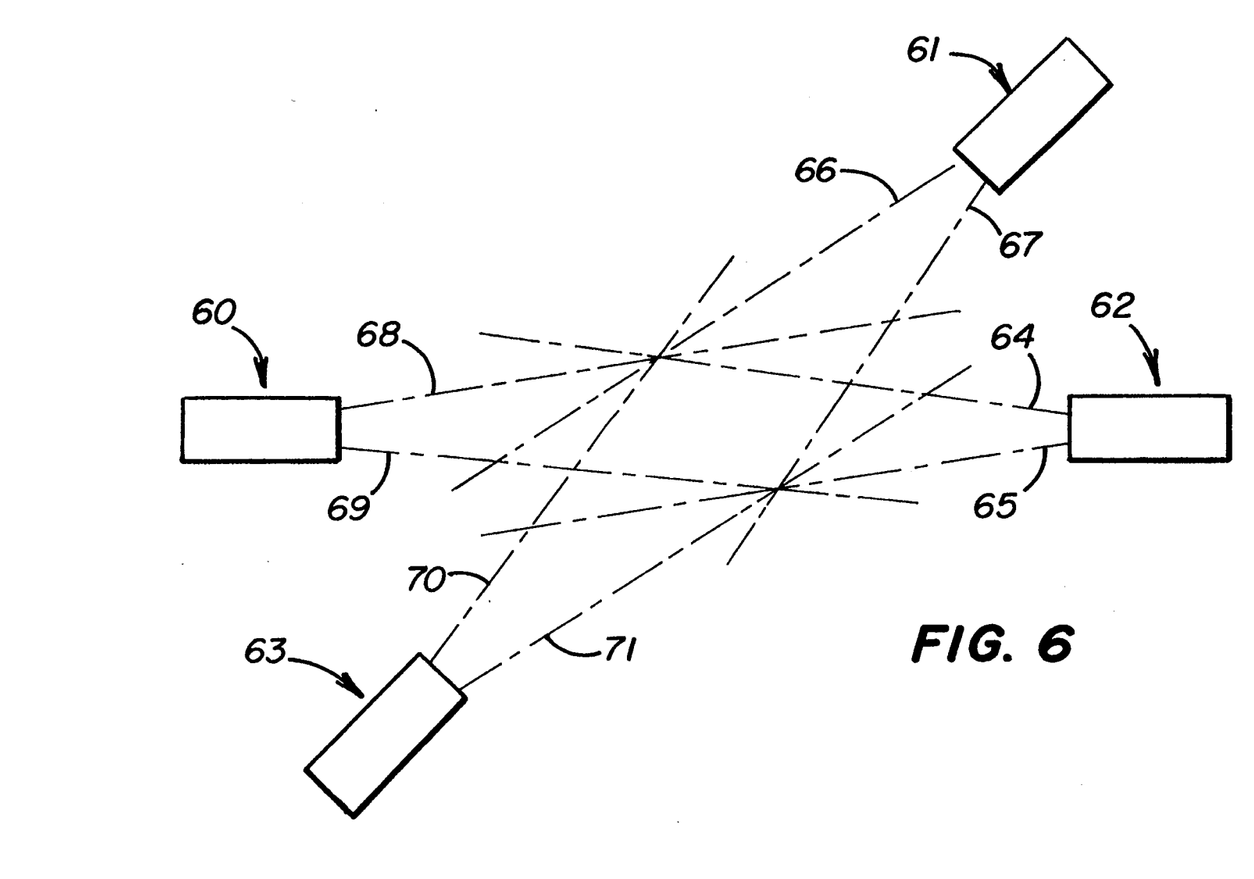

FIG. 6 shows a four-headed configuration. Transmit head 60 is defined by light rays 68 and 69, transmit head 63 is defined by light rays 70 and 71, receiver light head 61 is defined by light rays 66 and 67 and receiver head 62 is defined by light rays 64 and 65. Transmit head 60 is arranged coaxially with receiver head 62, and transmit head 63 is arranged coaxially with receiver head 61. These transmit/receive pairs then have their axes arranged with respect to each other such that the axes cross and subtend an obtuse angle, which defines the angular scattering coefficient angle. There is a common volume of intersection which is represented by the intersection of the light rays as shown in the figure. The scattering occurs substantially within this volume, and it is desirable to control the spatial configurations adequately.

The operation of the preferred embodiment system, as shown in FIG. 6 is as follows: Transmit head 60 and transmit head 63 are toggled on, back and forth. Only one transmit head is operating at any given time. Receiver heads 61 and 62 are always operating. When transmit head 60 is in an on state, receiver head 62 measures direct transmission, and receiver head 61 measures scattered transmission. When transmit head 63 is in an on state, receiver head 61 measures the direct transmission and receiver head 62 measures scattered transmission. There will, therefore, be two scattered measurements and two direct measurements. The resulting calculation for the forward scatter coefficient is therefore strengthened by virtue of statistical verification. In other words, the confidence level has been increased by a factor due to the redundant measurements.

Any individual component of the system may fail, and the unit will still be able to output a visibility measurement. When transmit head 60 fails, the system defined by transmit head 63 and receiver heads 61 and 62 will suffice to provide a forward scatter visibility measurement. Likewise with failures of any of the other heads. In addition, it will be immediately obvious when a head has failed because the other three heads will be able to determine the problem.

Figure 7:
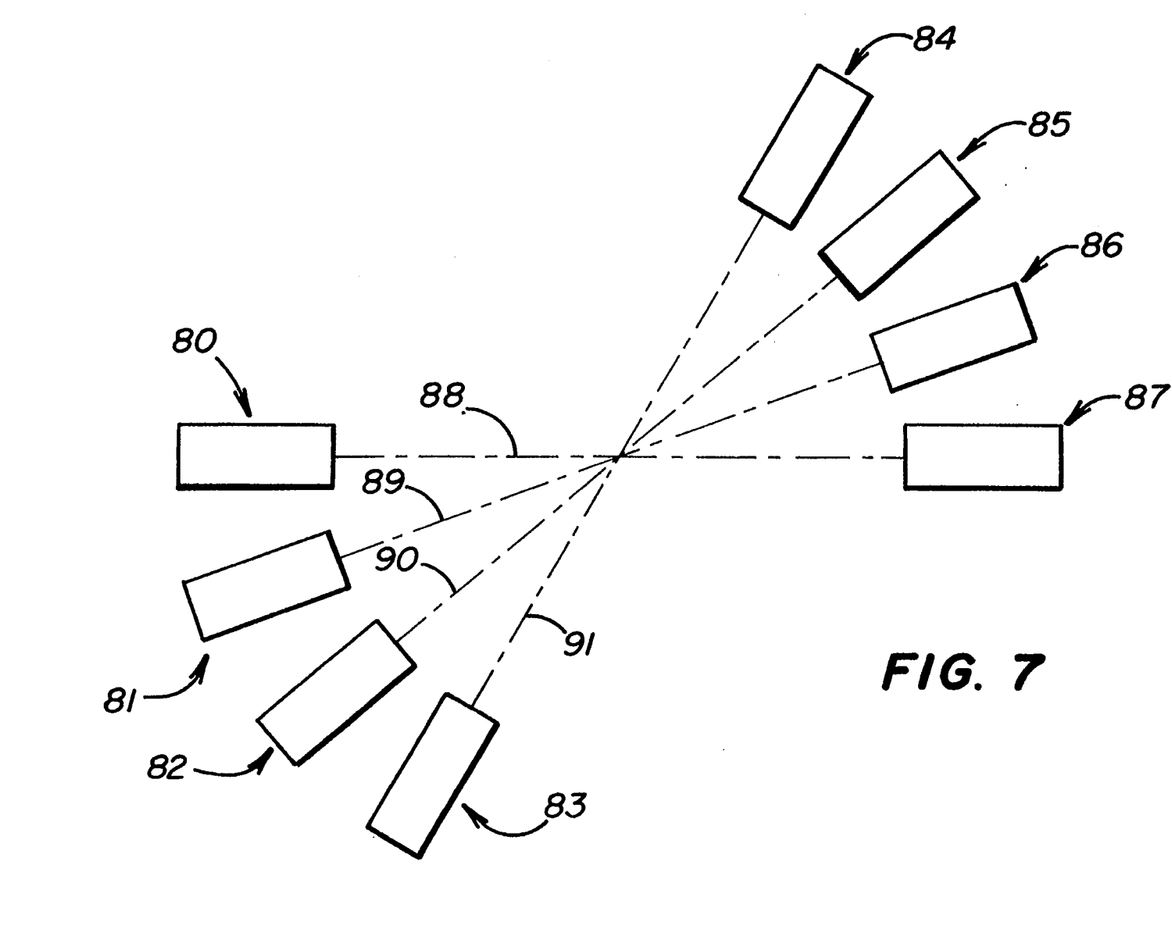
Figure 8:
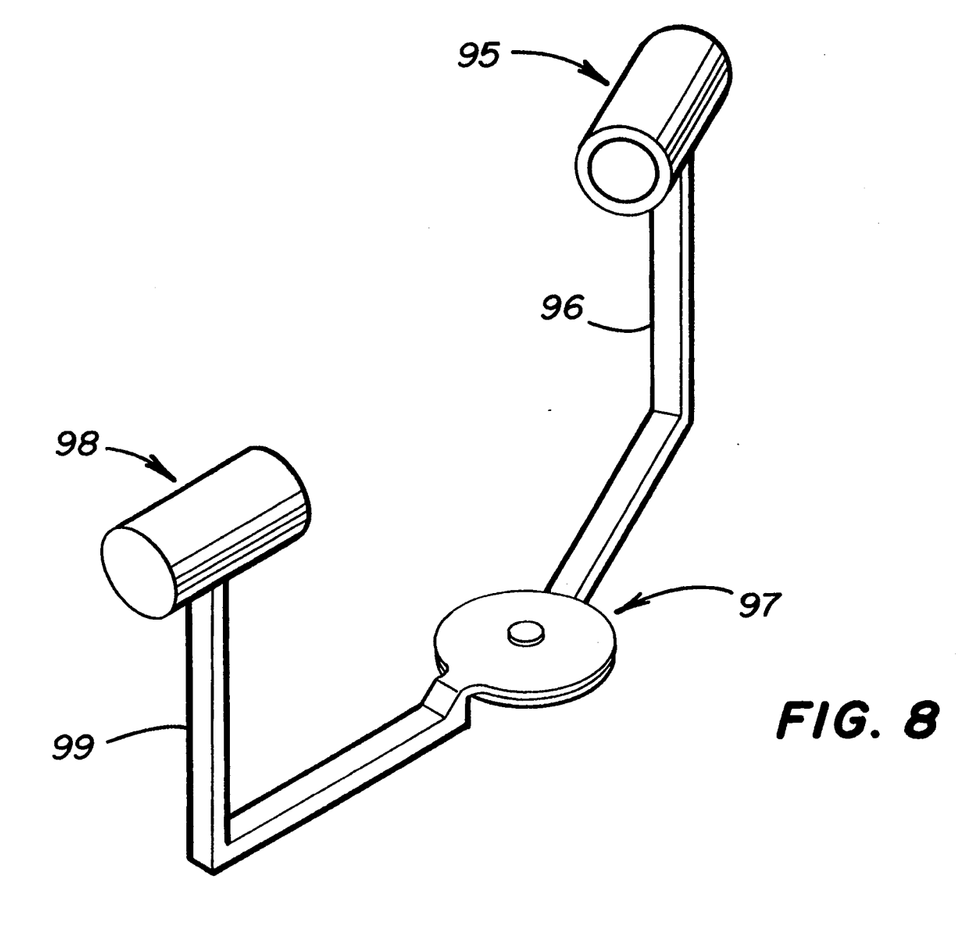

FIG. 7 shows a block diagram representation of a multiple scatter angle, redundant system configuration. Transmit head 80 is aligned coaxially, along axis 88, with receiver head 87. Transmit head 81 is aligned coaxially, along axis 89, with receiver head 86. Transmit head 82 is aligned coaxially, along axis 90, with receiver head 85 and transmit head 83 is aligned coaxially, along axis 91, with receiver head 84. The four pairs of elements are then arranged so that their respective axes intersect at a common, substantially central, point. The defining light rays are not shown in this figure, but it is clear that the central axes essentially define the light cones. There is therefore a central volume of aerosol which provides the scattering medium appropriate to the system which is defined by the common intersection of the light cones.

Operation of the system is as follows: Only one transmit head is operating at any given time. All four receiver heads are always operating. When transmit head 80 is in an on state, receiver head 87 measures the direct transmission. This value is used, as before, to calibrate or correct the scattered transmissions. When transmit head 80 is in an on state, receiver head 86 measures the scattering coefficient for the appropriate angle, as shown in the figure. Receiver head 85 measures the scattering coefficient for a steeper angle, as shown, and receiver head 84 measures an even steeper angular coefficient.

A knowledgeable practitioner in the art will quickly realize that with each transmit head operation state, there will be four receiver head amplitudes measured. These amplitudes will correspond variously to direct transmission, and three scattered transmissions. For the four-headed system shown in FIG. 7, there will be a total of sixteen measurements made. If the obtuse angles of separation between the optical axes are the same, there will be redundant measurements which may be statistically combined to obtain a higher level of confidence, as well as a level of failure recognition. When the obtuse angles vary, the system will be able to calculate scattering coefficients for a wide range of scattering angles. Since the angular scattering coefficient varies with respect to certain parameters of the aerosol gas, the multiple scatter angle, redundant system will provide an extra dimension of analysis and output information over a system with a single scattering angle measurement.

It will be obvious to those versed in the state of the art that any number of multiple scattering angles will be feasible by appropriately configuring the spatial layout of the receiver/transmitter pairs. Any amount of system reliability may be programmed by configuring the system with an appropriate number of receiver/transmitter pairs. The system is not restricted to operation in the forward scatter mode of operation since any angular orientations may be achieved.

FIG. 8 shows a perspective representation of a generalized angular scattering coefficient configuration. Transmit head 98 propagates a cone of light along an optical axis. Receiver head 95 receives a cone of light along an optical axis. Mast arms 96 and 99 appropriately support the heads, respectively. Pivot point 97 provides a rotatable connection between mast arm 96 and mast arm 99. Pivot point 97 allows the optical axes of transmitter 98 and receiver head 95 to cross at an invariable point, but the angle of crossing may continuously vary. Pivot point 97 may be effected by either automatic electrical or mechanical, manual means. When the angle of intersection is zero degrees, the system is in a straight-through, direct transmission configuration. As the angle is varied, the different scattering amplitudes measured may be compared to the direct amplitude and the data is appropriately corrected for errors.

By using the measurements made with the configuration shown in FIG. 8, a detailed analysis of constituent particle size will be feasible. By configuring two identical systems as shown in FIG. 8, but with different optical energy frequencies, it will be possible to take this analysis a step further. It will be obvious to those versed in the art that a single system is achievable, with different wavelengths of optical energy, and appropriate optical components within the heads, that will measure the continuous angular scattering coefficients at several different wavelengths.

It will be apparent to those skilled in the art that the disclosed multiple angle, redundant forward scatter visibility sensor may be modified in numerous ways and may assume many embodiments other than the preferred forms specifically set out and described above. For example, a microprocessor may be added to the system to increase the fundamental calculation and reliability capabilities of the system. Numerous different optical configurations within the transmitter and receiver heads could readily be implemented by one of ordinary skill in the art to perform the functions specifically described above for forward scatter visibility measurement. A wide variety of spatial configurations may be configurable.

Although the preferred embodiment of the invention was described in connection with the detection of optically scattered energy, the sensing capability of the present invention may apply to many other types of sensing applications, for instance, in a fluid medium instead of a gaseous medium. Accordingly, it is intended by the appended claims to cover all such modifications of the invention which fall within the true spirit and scope of the invention.

What is claimed is:

1. A visibility sensor, comprising:
   an elongated support having a first end and a second end;
   a transmitter located at the first end of the elongated support and directing a generally conical beam of light along a first axis into a scattering medium which scatters the conical beam of light;
   a first receiver located at the second end of the elongated support and receiving the generally conical beam of light along the first axis; and
   a second receiver for receiving the scattered light along a second axis intersecting the first axis.

2. The visibility sensor of claim 1, wherein the transmitter includes:
   light generating means for providing the generally conical beam of light responsive to a power signal;
   power supply means, coupled to the light generating means, for supplying the power signal responsive to a modulated signal; and
   modulating means, coupled to the power supply means, for generating the modulating signal responsive to a control signal.

3. The visibility sensor of claim 1, wherein the first receiver and second receiver includes:
   an optical window for receiving the generally conical beam of light;
   focusing means for focusing the generally conical beam of light;
   optical filtering means, coupled to the focusing means, for reducing the noise of the generally conical beam of light; and
   transducer means, coupled to the optical filtering means, for generating a signal proportional to the energy of the generally conical beam of light.

4. The visibility sensor of claim 1, wherein the angle between the first axis and second axis is approximately 35 degrees.

5. The visibility sensor of claim 3, wherein the signal from the first receiver represents obfuscation of the optical window and the signal from the second receiver represents the amount of scattering particles in the scattering medium.

6. The visibility sensor of claim 5, wherein the visibility sensor further comprises:
   processor means, coupled to the transmitter, the first receiver and the second receiver, for providing a value of the scattering coefficients of the scattering medium responsive to the signals from the first receiver and second receiver.

7. A visibility sensor, comprising:
   an elongated support having a first end and a second end;
   a first transmitter located at the first end of the elongated support and directing a generally conical beam of light along a first axis into a scattering medium;
   a second transmitter directing a generally conical beam of light along a second axis the scattering medium which scatters the conical beam of light, wherein the second axis intersects the first axis; and
   a receiver located at the second end of the elongated support and receiving both the generally conical beam of light and scattered conical beam of light along the first axis.

8. The visibility sensor of claim 7, wherein the first transmitter and second transmitter includes:
   light generating means for providing the generally conical beam of light responsive power signal;
   power supply means, coupled to the light generating means, for supplying the power signal responsive to a modulated signal; and
   modulating means, coupled to the power supply means, for generating the modulating signal responsive to a control signal.

9. The visibility sensor of claim 7, wherein the receiver includes:
   an optical window for receiving the generally conical beam of light and the scattered conical beam of light;
   focusing means for focusing the generally conical beam of light and the scattered conical beam of light;
   optical filtering means, coupled to the focusing means, for reducing the noise of the generally conical beam of light and the scattered conical beam of light; and
   transducer means, coupled to the optical filtering means, for generating a signal proportional to the energy of the generally conical beam of light and scattered conical beam of light.

10. The visibility sensor of claim 7, wherein the angle between the first axis and second axis is approximately 35 degrees.

11. The visibility sensor of claim 9, wherein the receiver generates a first signal representing the obfuscation of the optical window responsive to the first transmitter generating a generally conical beam of light and the receiver generates a second signal representing the amount of scattering particles responsive to the second transmitter generating a generally conical beam of light into the scattering medium.

12. The visibility sensor of claim 11, wherein the visibility sensor further comprises:
   processor means, coupled to the first transmitter, the second transmitter, and the receiver, for providing a value of the scattering coefficients of the scattering medium responsive to the first and second signals.

13. A visibility sensor, comprising:
   a support;
   a plurality of transmitters, coupled to the support, wherein a first transmitter directs a generally conical beam of light along a first axis into a scattering medium which scatters the conical beam of light along a second and a third axis; and a plurality of receivers, coupled to the support, wherein a first receiver is positioned along the first axis and receives the generally conical beam of light, and wherein a second and a third receiver is positioned along the second and the third axis, respectively, to receive the scattered conical beam of light along the second axis and third axis.

14. The visibility sensor of claim 13, wherein the first transmitter includes:
light generating means for providing the generally conical beam of light responsive power signal;
power supply means, coupled to the light generating means, for supplying the power signal responsive to a modulated signal; and
modulating means, coupled to the power supply means, for generating the modulating signal responsive to a control signal.

15. The visibility sensor of claim 13, wherein the first receiver includes:
an optical window for receiving the generally conical beam of light;
focusing means for focusing the generally conical beam of light;
optical filtering means, coupled to the focusing means, for reducing the noise of the generally conical beam of light; and
transducer means, coupled to the optical filtering means, for generating a signal proportional to the energy of the generally conical beam of light.

16. The visibility sensor of claim 13, wherein the angle between a pair of adjacent axes is approximately 35 degrees.

17. The visibility sensor of claim 15, wherein the first receiver generates a first signal representing the obfuscation of the optical window responsive to the first transmitter generating a generally conical beam of light and the second receiver and third receiver generate a second signal and third signal, respectively, representing the amount of scattering particles responsive to the first transmitter generating a generally conical beam of light into the scattering medium.

18. The visibility sensor of claim 17, wherein the visibility sensor further comprises:
processor means, coupled to the plurality of transmitters and the plurality of receivers, for providing a value of the scattering coefficients of the scattering medium responsive to the first signal, second signal, and third signal.

19. A visibility sensor, comprising:
a transmitter for directing a generally conical beam of light along a first axis into a scattering medium which scatters the conical beam of light;
a receiver for receiving the generally conical beam along the first axis and a second axis, wherein the first axis intersects the second axis; and
positioning means, coupled to the transmitter and receiver, for determining the angle between the first axis and second axis.

20. The visibility sensor of claim 19, wherein the transmitter includes:
light generating means for providing the generally conical beam of light responsive to a power signal;
power supply means, coupled to the light generating means, for supplying the power signal responsive to a modulated signal; and
modulating means, coupled to the power supply means, for generating the modulating signal responsive to a control signal.

21. The visibility sensor of claim 19, wherein the receiver includes:
an optical window for receiving the generally conical beam of light;
focusing means for focusing the generally conical beam of light:
optical filtering means, coupled to the focusing means, for reducing the noise of the generally conical beam of light; and
transducer means, coupled to the optical filtering means, for generating a signal proportional to the energy of the generally conical beam of light.

22. The visibility sensor of claim 21, wherein a first signal from the receiver represents obfuscation of the optical window.

23. The visibility sensor of claim 22, wherein a second signal from the receiver represents the amount of scattering particles in the scattering medium.

24. The visibility sensor of claim 22, wherein the sensor further comprises:
processor means, coupled to the transmitter and the receiver, for providing a value of the scattering coefficients of the scattering medium responsive to the first signal and second signal.

25. A visibility sensor, comprising:
an elongated support having a first end and a second end;
a first light source located at the first end of the support and directing a generally conical beam of light along a first axis into a scattering medium which scatters the conical beam of light;
a second light source located at the first end of the support and directing a generally conical beam of light along a second axis into a scattering medium which scatters the conical beam of light;
a first light detector located at the second end of the support and receiving the generally conical beam of light along the first axis; and
a second light detector for receiving the scattered light along the second axis intersecting the first axis.

26. A visibility sensor, comprising:
an elongate support having a first end and a second end;
a light source located at the first end of the elongated support and directing a generally conical beam of light along a first axis into a scattering medium which scatters the conical beam of light;
a first light detector located at the second end of the elongated support and receiving the generally conical beam of light along the first axis; and
a second light detector for receiving the scattered light along a second axis intersecting the first axis.

* * * * *

UNITED STATES PATENT AND TRADEMARK OFFICE
CERTIFICATE OF CORRECTION

PATENT NO. : 5,373,367
DATED : December 13, 1994
INVENTOR(S) : Richard N. DeGunther and Wilbert I. Marsh It is certified that error appears in the above-indentified patent and that said Letters Patent is hereby corrected as shown below:

Claim 7, column 10, line 11, after "axis" and before "the", insert --into--.

Claim 8, column 10, line 21, after "responsive" and before "power", insert --to a--.

Claim 14, column 11, line 11, after "responsive" and before "power", insert --to a--.

Claim 26, column 12, line 51, change "elongate" to --elongated--.

Signed and Sealed this

Fourth Day of April, 1995

Attest:

BRUCE LEHMAN

Attesting Officer  Commissioner of Patents and Trademarks